United States Patent

Hadjicostis et al.

[11] Patent Number: 5,947,905
[45] Date of Patent: Sep. 7, 1999

[54] ULTRASOUND TRANSDUCER ARRAY PROBE FOR INTRALUMINAL IMAGING CATHETER

[75] Inventors: Andreas Hadjicostis, Love tree; Michael J. Zipparo, Parker; Lanette P. Westwood, Indian Hills, all of Colo.

[73] Assignee: Advanced Coronary Intervention, Inc., Englewood, Colo.

[21] Appl. No.: 08/951,060

[22] Filed: Oct. 15, 1997

[51] Int. Cl.⁶ .................................................. A61B 8/12
[52] U.S. Cl. ............................................. 600/463
[58] Field of Search .................. 600/459–471; 29/25.35; 310/334–336

[56] References Cited

U.S. PATENT DOCUMENTS

| | | |
|---|---|---|
| D. 347,896 | 6/1994 | Dickinson . |
| 3,938,502 | 2/1976 | Bom . |
| 4,505,156 | 3/1985 | Questo . |
| 4,543,960 | 10/1985 | Harui . |
| 4,571,520 | 2/1986 | Saito et al. .................. 310/327 |
| 4,841,977 | 6/1989 | Griffith . |
| 4,917,097 | 4/1990 | Proudian . |
| 5,027,659 | 7/1991 | Bele . |
| 5,109,861 | 5/1992 | Walinsky . |
| 5,186,177 | 2/1993 | O'Donnell . |
| 5,226,847 | 7/1993 | Thomas, III . |
| 5,257,629 | 11/1993 | Kitney . |
| 5,273,045 | 12/1993 | Chihara . |
| 5,402,793 | 4/1995 | Gruner . |
| 5,456,259 | 10/1995 | Barlow . |
| 5,465,726 | 11/1995 | Dickinson . |
| 5,509,827 | 4/1996 | Huppenthal . |
| 5,590,659 | 1/1997 | Hamilton . |
| 5,601,082 | 2/1997 | Barlow . |
| 5,630,421 | 5/1997 | Barlow . |

FOREIGN PATENT DOCUMENTS 0 671 221 A2  9/1995  European Pat. Off. .

OTHER PUBLICATIONS

A. Gachagan, 1996 IEEE Ultrasonics Symposium, Construction and Evaluation of a New Generation of Flexible Ultrasonic Transducers, 1996.
Loriann L. Ries, 1996 IEEE Ultrasonics Symposium, Phase Aberration Correction in Two Dimensions With An Integrated Deformable Actuator/Transducer, 1996.
Charles D. Emery, 1996 IEEE Ultrasonics Symposium, Signal To Noise Ratio of Hybrid Multilayer/Single Layer 2–D Arrays, 1996.
Richard E. Davidsen, 1996 IEEE Ultrasonics Symposium, A Multiplexed Two–Dimensional Array For Real Time Volumetric and B–Mode Imaging, 1996.
Stephen W. Smith, 1995 IEEE Ultrasonics Symposium, Update On 2–D Array Transducers For Medical Ultrasound, 1995.
Loriann L. Ries, 1995 IEEE Ultrasonics Symposium, Phase Aberration Correction in Two Dimensions Using A Deformable Array Transducer, 1995.
J.E. Piel, Jr., 1994 Ultrasonics Symposium, MHZ Pediatric Phased Array Transesophageal Endoscope, 1994.
William C. Black, Jr., 1994 IEEE Journal of Solid–State Circuits, vol. 29, No. 11, CMOS Chip for Invasive Ultrasound Imaging, Nov. 1994.

*Primary Examiner*—Francis J. Jaworski
*Attorney, Agent, or Firm*—Gibson, Dunn & Crutcher LLP

[57] ABSTRACT

An ultrasound transducer array probe for intraluminal ultrasound imaging is situated on a distal end of a catheter. The probe has a flex circuit that accepts terminations from a plurality of coaxial cables admitted through the catheter, and electrically conveys these signals to integrated circuits and an ultrasound array acoustic stack, preferably having seventy-two elements. The circuit has more than one layer of metal tracings to support complicated electrical interconnections. The acoustic stack preferably includes two quarter-wave matching layers and an acoustic backing layer composed of urethane, $AlN_3$, tungsten trioxide, and microballoons. The flex circuit can be formed of two sections that are joined during manufacture.

33 Claims, 5 Drawing Sheets

ULTRASOUND TRANSDUCER ARRAY PROBE FOR INTRALUMINAL IMAGING CATHETER

FIELD OF THE INVENTION

The present invention relates to the field of intraluminal ultrasound imaging devices, and more particularly to a transducer array probe for transmitting and receiving ultrasound signals used in forming images.

BACKGROUND

Ultrasonic imaging from within the body of a patient has been used for some time, as for example as a preliminary step in the treatment of heart disease. While alternative methods of sensing the condition of diseased vasculature exist, such as the injection and monitoring of radiopaque dyes, ultrasound is currently the most promising technology for accurately viewing the interior of a body in real time and in a non-destructive manner.

Such imaging techniques are particularly useful in connection with an angioplasty device that removes a built-up deposit within a lumen. Successful removal depends upon accurately locating the deposit in relation to the device. It is desirable that the resolution of a visualization technique be commensurate with, or better than, the degree of resolution of the ablation device. The present invention has particular utility with high resolution ablation devices. An example of such a device is described in U.S. Pat. Nos. 5,626,576 and 5,454,809, commonly owned with the present invention. In such a device, radio frequency current is selectively deployed around the circumference of a lumen such as a coronary artery, depending upon the position of the occlusive material. The imaging used with such a device should enable the user to determine the circumferential position of the deposit. In general, prior art ablation techniques have not required the visualization resolution provided by the present invention.

In an in vivo ultrasound imaging system, either a rotating single transducer element or an array of piezoelectric transducer elements residing on a catheter are introduced into a body. The element(s) are excited at ultrasound frequencies to transmit acoustical waves, and receive echos as the acoustical waves reflect from the surrounding material. The echos provide electrical signals which are processed to form the ultrasound image.

Previous in vivo ultrasound images have included a number of limitations. The simplest systems use a mechanical scanning system. A flexible drive cable rotates a single element to scan a cross sectional image of a lumen. Problems associated with mechanical systems include mechanical breakdown, image jitter and smear, limitations due to fixed transmit and receive focus, and low image resolution away from the focal point. Existing electronic imaging systems address some of the above impediments but are still believed to have associated problems such as low signal to noise ratio and/or low frame rate (depending on whether multiple samples of element pulses are taken), reduced tissue penetration (because of relatively low transmit energy), narrow bandwidth pulses, and sub-optimal axial and lateral resolution (because only one matching layer is used). A modern electronic imaging system is described in international application Publication No. WO 97/23865 (Endosonics). The device of said application may serve its intended purpose, but does not disclose a technique to include complicated circuitry on a flexible circuit, and does not provide optimal acoustic matching or backing. A similar electronic imaging system is disclosed in European Patent Application No. 0 671 221 A2 (Intravascular Research Limited). The present invention effectively addresses the above problems through numerous design advances.

More complex electronic processing enables superior ultrasound imaging. Such processing requires a number of advances in the circuitry and associated components. In particular, incorporating a greater number of transducer elements is advantageous since it provides improved flexibility in manipulating a transmit and receive aperture, and element phasing. Also, the incorporation of advanced design IC chips improves signal to noise ratio and penetration and frame rate. The use of an extra matching layer improves signal bandwidth and axial resolution. Without limitation, it is an object of the present invention to satisfy the above mentioned imaging criteria and thereby advance the field of intravascular ultrasound imaging.

The transducer array probe described herein has particular application with the MUX/pre-amplifier ASIC described in co-pending application No. 08/950,900 titled "Intravascular Ultrasound Mixed Signal Multiplexer/Pre-Amplifier BiCMOS ASIC", filed under attorney docket no. 010848-0015 contemporaneously herewith. However, it is not limited to such a device, and is operable using other circuitry.

All documents referred to herein are hereby incorporated by reference to the extent they contain information necessary or helpful to an understanding of the present invention.

SUMMARY

According to an aspect of the present invention an ultrasound transducer array probe for an imaging catheter is provided, the probe being generally cylindrical and defining an interior direction towards an axis and an exterior direction away form the axis. The probe has a flexible circuit substrate having connecting means to physically and electrically receive a plurality of coaxial cables, the flexible circuit supporting two metal layers, each of the metal layers having traces thereon; a plurality of micro-capacitor structures in electrical communication with at least some of the coaxial cables that are power supply cables; a plurality of multiplexer/pre-amplifier integrated circuits in electrical communication with the micro-capacitor structures; a plurality of piezoelectric ultrasound array elements in electrical communication with the integrated circuits, the electrical communication being through at least some of the traces on the metal layers; and an acoustic backing layer acoustically engaged with the piezoelectric elements, the acoustic backing layer being interior with respect to the piezoelectric elements.

According to further aspects of the invention, the micro-capacitor structures are formed from a combination of discrete capacitors and the discrete capacitors are aligned with the integrated circuits.

According to further aspects of the invention, a primary acoustic layer is provided exterior to the piezoelectric layer; wherein the piezoelectric layer is exterior to the flexible circuit substrate. The primary acoustic matching layer may be an electric insulator.

According to further aspects of the invention, the array probe includes an exterior film layer, the exterior film layer being exterior to the primary acoustic matching layer and being composed of a bio-compatible material. Both the primary acoustic matching layer and the exterior film layer are preferably substantially quarter wave matching layers, wherein the primary acoustic matching layer has an acoustical impedance of about 7–15 MRayls and the exterior film layer has an acoustical impedance of about 2–6 MRayls. The exterior film layer may be composed of polyurethane, polyethylene shrink wrap, or other materials. As an alternative embodiment, only one matching layer is used. Such matching layer is an exterior layer, and so is con-conductive and bio-compatible, and preferably has an impedance of between 2.5–7.5 MRayls.

According to further aspects of the invention, the probe includes a radio-opaque marker, and a guide wire, the guide wire being substantially aligned with the axis of the of the probe.

According to further aspects of the invention, at least some of the metal traces on each of the two metal layers supported by the flexible circuit are electrically interconnected to at least some of the metal traces on the other metal layer through via holes. The traces on one of the metal layers are generally vertical and the traces on the other metal layer are generally horizontal, the vertical and horizontal directions being arbitrary with respect to the probe and relative to each other, whereby the traces on the two layers are generally perpendicular with respect to one another. The two metal layers are separated by an insulating layer.

According to further aspects of the invention, the flex circuit is constructed of two distinct sections that are joined during manufacture. One flex circuit section is electrically connected to the coaxial cables, the micro-capacitor structures, and the multiplexer/pre-amplifier integrated circuits; and the other flex circuit section is electrically connected to the piezoelectric ultrasound array elements. The two flex circuit sections may be joined by depositing a conductor on at least a portion of the flex circuit sections, the joining of the flex circuit sections including separating the traces on the flex circuit metal layers. The probe may include a radio-opaque marker, wherein the radio-opaque marker extends generally from the piezoelectric array to the multiplexer/pre-amplifier integrated circuits, whereby the joined flex circuit sections are stabilized. The probe may include support members beneath the multiplexer/pre-amplifier integrated circuits.

According to further aspects of the invention, a portion of the flexible substrate is exterior to the second acoustic matching layer and is the most exterior layer of the probe, and the portion of the flexible substrate serves substantially as a quarter wave matching layer.

According to further aspects of the invention, the acoustic backing layer a filled urethane compound having an acoustical impedance of between 2.5–6 MRayl.

DETAILED DESCRIPTION

The present invention relates to the field of electronic devices and more particularly to an ultrasound imaging probe for insertion into a lumen of a human body. The purpose of the probe is to receive and convert electrical pulses to mechanical pulses and vice versa, in a manner that is useful in forming an image.

The present invention is described below in connection with two primary embodiments: one having an "external" flex circuit and another having an "internal" flex circuit. Figure and reference numerals for the first embodiment generally have an "a" suffix and for the second embodiment have a "b" suffix; some figures and references are equally applicable to both embodiments. It should be understood that the description below generally applies to both embodiments unless otherwise noted. The "internal" flex embodiment is described first.

Figure 1:
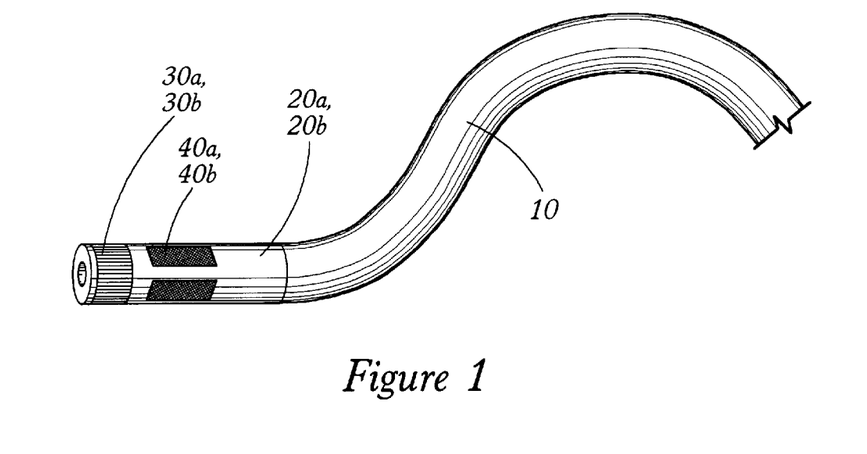
FIG. 1 is a schematic representation of an ultrasonic transducer array probe according to an embodiment of the present invention, situated on a catheter.

Referring to the schematic view of FIG. 1, the probe includes a flex circuit 20a having a flexible substrate constructed of polyimide or similar material, and an ultrasound array 30a residing at a distal end of a catheter 10. The catheter 10 is insertable within and along the lumen until the ultrasound array 30a is at a desired imaging site. In an exemplary use, the lumen may be a coronary artery of a patient suffering from coronary heart disease. However, the present invention is not limited to coronary applications, and may be used within any lumen of the body and even for extracorporeal imaging. For coronary use, the external diameter is preferably about 1.19 mm (3.5 F), it being understood that other sizes may be used for other lumens.

The processing of electrical signals within the transducer probe array is preferably performed by four MUX/preamplifier ASICs 40*a* (application specific integrated circuits, referred to as MUXes herein for convenience as multiplexing is a primary purpose of the integrated circuits), as described in the co-pending application No. 08/950,900 titled "Intravascular Ultrasound Mixed Signal Multiplexer/ Preamplifier BiCMOS ASIC," and the array probe is described as if such MUXes 40*a* are present. It should be understood, however, that other circuitry could be used instead of the cited MUXes 40*a*, with modifications to the flex circuit 20*a* and array probe as may be appropriate.

Figure 2:
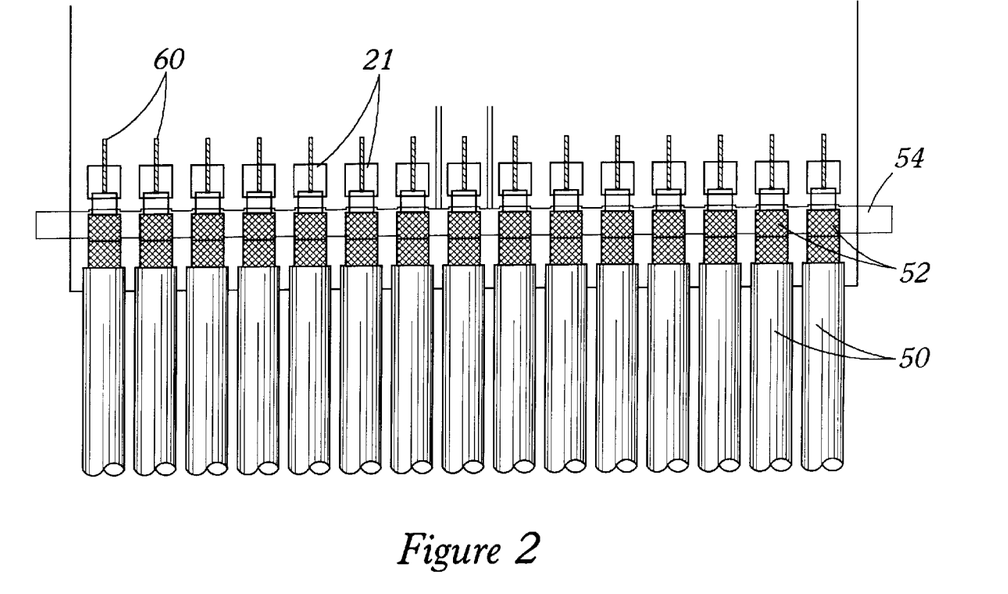
FIG. 2 is a plan view showing the coaxial bundle of the present invention in a flattened view.
Figure 3A:
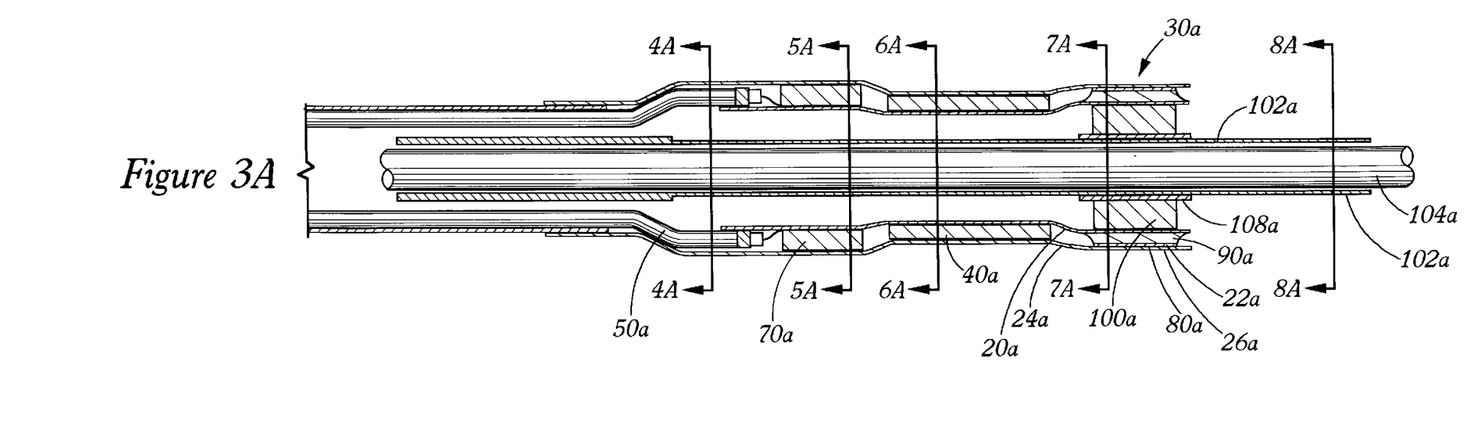
FIG. 3A is a longitudinal sectional view of the transducer array probe according to FIG. 1, showing an embodiment having an interior flex circuit.

The array flex circuit 20*a* receives electrical input from a plurality of coaxial cables 50*a* (see FIGS. 2 and 3A). In a representative embodiment, eleven coaxial cables 50*a* of 46 gauge are used. Four of the coaxial cables transmit analogue signals (i.e., electrical signals that are either being transmitted to or received from an ultrasound array acoustic stack 30*a*), five of the cables transmit digital signals that select which elements of the array 30*a* are active, and two of the cables supply power. In another embodiment, shown in the cross-sectional view of FIG. 4A, fifteen coaxial cables 50*a* are provided: the eleven described above and an additional four cables for supplying RF current to electrodes (not shown) to ablate obstructive material within the lumen. The RF cables do not form an integral part of the present invention, but are included to show a preferred application.

Figure 4A:
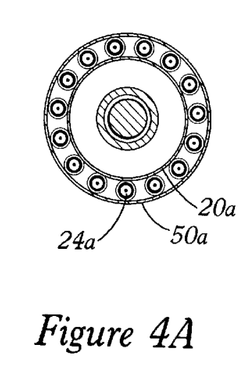
FIG. 4A is a sectional view taken along the line 4A–4A of FIG. 3A, showing the coaxial bundle in the cylindrical configuration.
Figure 4B:
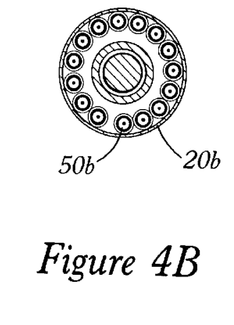
FIG. 4B is a sectional view taken along the line 4B—4B of FIG. 3B, showing the coaxial bundle in the cylindrical configuration.

The connection between the coaxial cables 50*a* and the flex circuit 20*a* is shown in FIG. 2, wherein the cables 50*a* are shown linearly disposed for purposes of illustration and explanation, it being understood that the cables are formed in a generally cylindrical configuration in the operative embodiment (as shown in FIGS. 4A and 4B). In FIG. 2, no suffixes are used, as the components are identical in the "internal" and "external" embodiments and the disclosure is equally applicable to both. A layer of outer insulation is removed from each cable 50 to expose a portion of outer conductor 52. Each of the outer conductors 52 are attached to a ground bus 54, which in turn is connected to the MUXes 40. Each cable 50 has an inner conductor 60 terminated to an individual pad 21 on the flex circuit 20*a*. The pad 21 is electrically connected to an appropriate input of one of the MUXes 40.

Turning now to the longitudinal sectional view of FIG. 3A, other features of the probe are described. A notable feature is the inclusion of power signal smoothing capacitors. Two of the cables 50*a* are power supply cables. The two power cables are each electrically connected to a separate micro-capacitor structure 72*a* (see FIGS. 5A and 5B). In a preferred embodiment, each micro-capacitor structure 72*a* is 1600 pF and is formed by a parallel connection of two 800 pF capacitors 70*a*. At the operative ultrasound frequencies (around 20 MHZ), the capacitor structures 72*a* have an impedance of less than 10 Ω. The micro-capacitor structures 72*a* serve as power conditioners which reduce the noise level on the power supply lines.

Figure 5A:
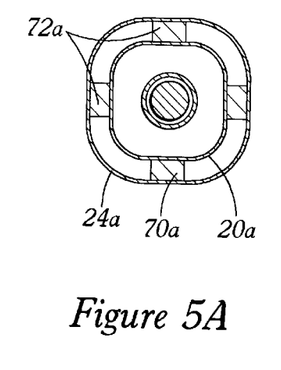
FIG. 5A is a sectional view taken along the line 5A—5A of FIG. 3A, showing the capacitors.
Figure 5B:
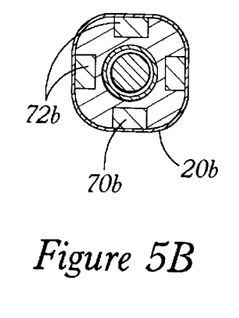
FIG. 5B is a sectional view taken along the line 5B—5B of FIG. 3B, showing the capacitors.
Figure 6A:
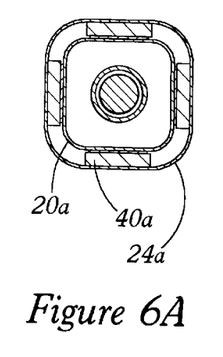
FIG. 6A is a sectional view taken along the line 6A—6A of FIG. 3A, showing the integrated circuits.
Figure 6B:
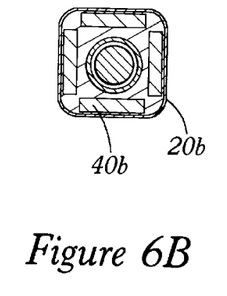
FIG. 6B is a sectional view taken along the line 6B—6B of FIG. 3B, showing the integrated circuits.

As shown in the radial cross sections of FIG. 5 (taken through the capacitors 70*a*) and FIG. 6 (taken through the MUXes 40*a*), the micro-capacitors 70*a* are aligned with the MUXes 40*a* around an exterior circumference of the flex circuit 20*a*. This alignment facilitates the formation of the probe into a generally cylindrical shape, which can then be mounted on the tip of the catheter 10 as shown in FIG. 1.

Figure 7A:
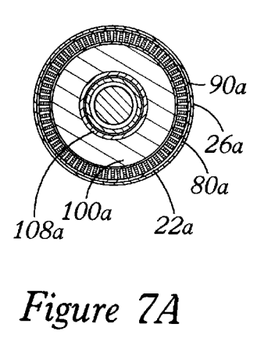
FIG. 7A is a sectional view taken along the line 7A—7A of FIG. 3A, showing the ultrasound array (i.e., the acoustic stack).
Figure 7B:
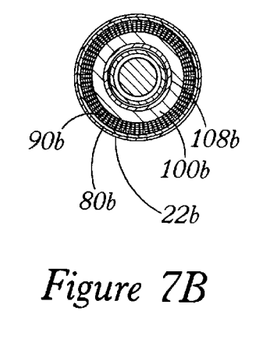
FIG. 7B is a sectional view taken along the line 7B—7B of FIG. 3B, showing the ultrasound array (i.e., the acoustic stack).
Figure 8A:
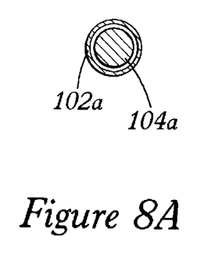
FIG. 8A is a sectional view taken along the line 8A—8A of FIG. 3A, showing the guide wire and innermost catheter tubing surrounding the guide wire.
Figure 8B:
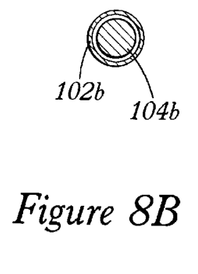
FIG. 8B is a sectional view taken along the line 8B—8B of FIG. 3B, showing the guide wire and innermost catheter tubing surrounding the guide wire.

The analogue signals are transmitted from the MUXes 40*a* to the ultrasound array 30*a* (also referred to herein as the "acoustic stack"), which is shown in radial cross section in FIG. 7. The array 30*a* includes the following structure, generally described from the exterior of the device towards the interior: an exterior layer of polyurethane film 24*a* (the section of the exterior layer 24*a* that encloses the acoustic stack 30*a* (and forms part of the stack itself) is separately designated 26*a* for clarity) ; a primary acoustic matching layer 80*a*, a piezoelectric layer 90*a*, the flex circuit 20*a* (the portion of the flex circuit 20*a* within the acoustic stack being separately designated 22*a*) which serves as the substrate for the electrical connections, acoustic backing material 100*a*. A radio-opaque marker band 108*a* is preferably within the stack 30*a*.

Both the exterior layer 26*a* and the primary acoustic matching layer 80*a* are quarter-wave matching layers to match the acoustic impedance of the piezoelectric material (about 30 MRayl) to that of human tissue (about 1.5 MRayl). The parameters determining acoustical response are material composition and thickness. In a preferred embodiment, the acoustic stack 30*a*, including the piezoelectric elements, flex circuit, primary matching layer, and backing material is about 175 $\mu$m thick). The flex circuit 22*a* is about 25 $\mu$m thick. The primary acoustic matching layer 80*a* is about 60 $\mu$m thick. The primary matching layer 80*a* may be glass, porcelain, aluminum, filled (iron oxide) epoxy, or possibly other materials.

The use of two quarter-wave matching layers (the exterior layer 24*a* and the primary matching layer 80*a*) is advantageous in that it provides a broader bandwidth than a single matching layer, and further provides for more efficient transmission of acoustical energy, i.e., better sensitivity. Preferably, the exterior layer 24*a* has an acoustical impedance of about 2 to 6 MRayls, and the primary acoustic matching layer 80*a* has an acoustical impedance of about 7–15 MRayls. Other known systems purporting to have two matching layers in fact have two layers of similar impedance characteristics, which does not result in optimal matching.

The piezoelectric layer 90*a* may be of any material commonly used for such purposes, e.g., lead zirconate titanate, and is preferably about 60 to 100 $\mu$m thick. Other possible materials include, for example, single crystal relaxor ferroelectrics such as lead magnesium niobate-lead titanate (PMN-PT), and lead zinc niobate-lead titanate (PZN-PT).

The array is preferably composed of seventy-two individual elements, formed by dicing the piezoelectric layer 90*a* and the primary matching layer 80*a*. The flex circuit 22*a* is preferably not diced, as this maintains the structural integrity to physically support the array 30*a*; however, it may be possible to partially dice the flex circuit layer 22*a* while maintaining acceptable structural integrity.

Beneath (i.e., towards the interior of the structure) the flex circuit 22*a* layer 90*a* is a layer of acoustic backing material 100*a*, preferably about 0.15 mm thick. While any of a number of backing materials may be used, the present invention preferably utilizes a highly absorbent compound, the use of which as a backing material is believed to be previously unknown. The specific composition is:

| | |
|---|---:|
| A. CIBA RP 6400 Part H | 2.8 grams |
| B. CIBA RP 6400 Part R | 0.28 g |
| C. Tungsten Trioxide Powder | 1.53 g |
| D. AlN$_3$ Powder (having a particle size of 2.5 to 4 microns) | 0.191 grams |
| E. EMERSON CUMMING | 0.38 grams |

("Eccospheres" ASDT-28)

The preferred processing steps are:

1. mix C, D, and E gently and thoroughly;

2. add A and mix until consistent color is achieved;
3. add B and mix thoroughly;
4. place mixture in vacuum environment for about 10–15 minutes so as to de-air the mixture; and
5. cure mixture at room temperature for about 48 hours.

The use of any brand names is simply for convenience of reference and to describe a particular compound created by the inventors, it being understood that generic equivalents may be substituted. Urethane by itself (such as the CIBA RP 6400 specified above) may be an acceptable backing layer. However, urethane by itself does not have an optimal acoustic impedance (on the order of 1.5–2.2 MRayl) for backing material. The impedance of the above composition falls in the desired range of 2.5–6 MRayl. The "Eccospheres" may be replaced with other micro-balloons.

Absorption tests of the above material have shown that it is highly suitable as a backing material. The tungsten trioxide powder and the microballoons scatter acoustical pressure and raise the acoustical impedance of the compound. While not being bound to any particular theory, it is believed that the relatively differing acoustical parameters of the tungsten trioxide powder and the microballoons have a complementary effect; the tungsten trioxide powder raises the impedance of the backing material 100a while the microballoons raise the attenuation. The $AlN_3$ powder serves as an efficient thermal conductor within the compound. The above compound is known to provide excellent results, but the present invention is not limited to the specifically disclosed compounds or ratios. Rather, in light of this disclosure, it may be expected that other filled urethane compounds (i.e., a compound having a primary component of urethane and additional acoustical property-affecting compounds added thereto) may be used, most effectively when the urethane is filled so that its acoustical impedance is within the range of 2.5 to 6 MRayls.

A purpose of the polyurethane film 24a is to maintain the structure of the interior layers and to provide an inert exterior surface that is bio-compatible with human (or other animal) body tissue. Another purpose of the film 24a is to act as a second quarter wave matching layer in the acoustic stack 30a, as described above. The polyurethane layer 24a extends from a position covering a portion of the cables 50a, to over the acoustic stack 30a. Polyurethane could be replaced with other bio-compatible materials having similar acoustical properties, and is simply one such material. Another such material is polyethylene tubing, and particularly shrink tubing. Yet another such material is filled silicone elastomers, such as "RTV" (General Electric).

Figure 3B:
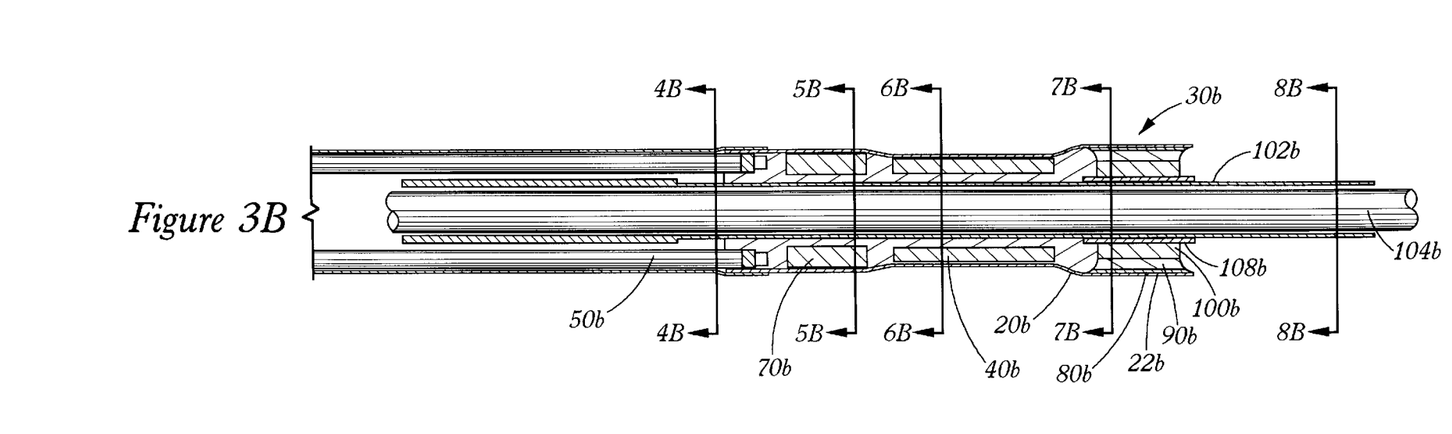
FIG. 3B is a longitudinal sectional view of the transducer array probe of FIG. 1, showing an embodiment having an exterior flex circuit.

The embodiment of the invention having an "exterior" flex circuit 20b is now described, with reference to the longitudinal sectional view of FIG. 3B, and the corresponding radial sectional views of FIGS. 4B–8B. The probe has coaxial cables 50b, power line conditioning capacitors 70b (and parallel combinations thereof 72b), and integrated circuits (MUXes) 40b corresponding to the "internal" embodiment. However, a flex circuit 20b replaces the polyurethane layer 24a as the exterior layer over these components. As with the internal embodiment, the flex circuit 20b has the function of forming the electrical interconnections between the coaxial cables, capacitors, integrated circuits, and piezoelectric elements. Further, the flex circuit 20b acts as a secondary acoustic matching layer, similar to the polyurethane layer 24a described above in connection with the internal flex circuit embodiment.

The primary difference in the embodiment is the acoustic stack, referred to generally as 30b. The structure, described from the exterior of the device inwards, is: the flex circuit 20b (the portion of the flex circuit 20b that is within the acoustic stack 30b being designated 22b); a primary acoustic matching layer 80b, a piezoelectric layer 90b, and an acoustic backing layer 100b. The composition, dimensions, and function of these layers is generally as described above in connection with "internal" embodiment. A primary distinction is that the flex circuit 22b serves as the second matching layer.

In another version of the "interior" embodiment, the primary acoustic matching layer 80b is eliminated, and the flex circuit 22b serves as a single matching layer. In such version, the flex circuit 22b is preferably selected so that it is has an impedance of between about 2.5–7.5 MRayls.

The "interior" embodiment has several advantages. The electrically active layer, i.e., flex circuit 22a, is shielded from the body of the patient somewhat more than in the "exterior" embodiment, possibly decreasing the risk of electric shock. (This is not to imply that the risk of shock is necessarily unreasonably high in the "interior" embodiment.) Further, the primary matching layer 80a need not be electrically conductive, as the flex circuit 22a is in direct contact with the piezoelectric layer 90a. This is particularly advantageous in that it may be substantially easier to bond a non-conducting primary matching layer 80a to the piezoelectric elements 90a.

The interior embodiment may improve SNR as the flex circuit 22a is interior and is further shielded by the exterior components. Otherwise, the flex circuit 22a can undesirably act as an antenna.

The interior embodiment may further provide advantages for the bonding and mechanical stability of the piezoelectric layer 90a. The layer 90a is firmly bonded to the flex circuit 22a, which prevents the diced elements from moving relative to one another when the device is cylindrically formed. Otherwise, the layer 90a may be somewhat less securely bonded to the urethane, which can stretch and undesirably allow relative motion.

The "exterior" embodiment may be advantageous in that the flex layer 20b serves as the physical exterior layer, the electrical interconnecting layer, and a matching layer; thus a somewhat thinner profile may be possible.

Figure 9:
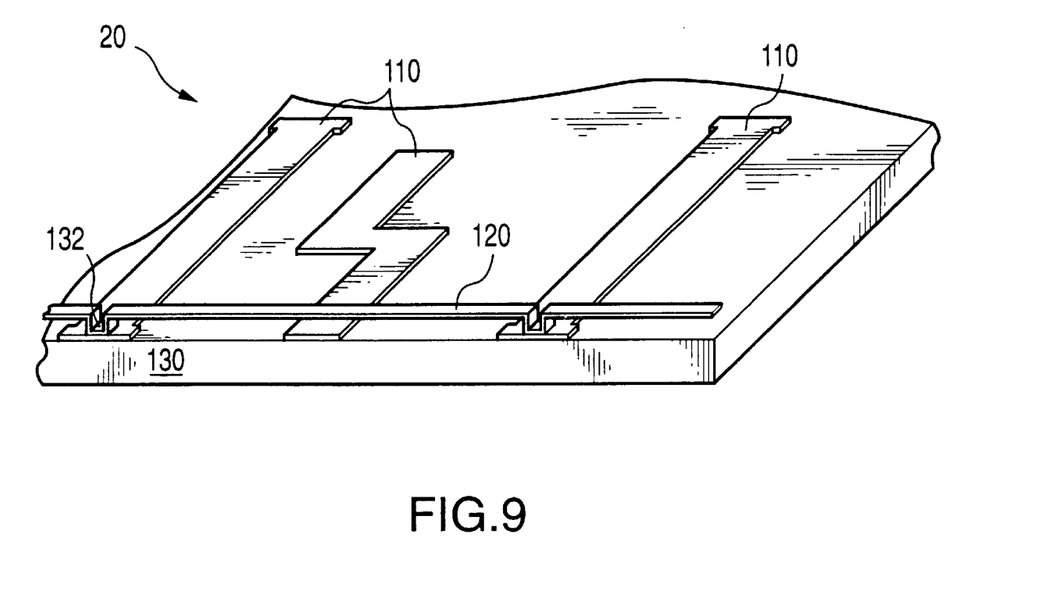
FIG. 9 is a perspective view of a section of a flex circuit according to the present invention, showing the first and second metal layers and associated components.
Figure 10:
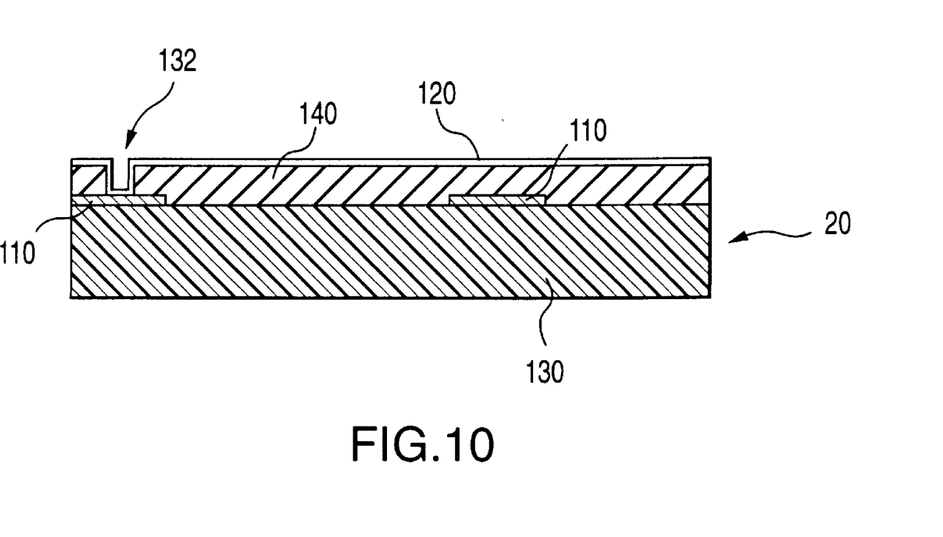
FIG. 10 is a sectional view of the flex circuit of FIG. 1, showing the first and second metal layers and associated components.

Another feature of the invention, generally applicable to both the "interior" and "exterior" embodiments (hence no suffixes "a" or "b" are used), is that the flex circuit 20 has two metal (conductor) layers, and two dielectric layers. This is unlike known flexible circuits that, at least in the field of intravascular imaging, have only one metal layer. The two layer flex circuit concept can be understood with reference to the perspective view of FIG. 9 and the cross-sectional view of FIG. 10. The flex circuit 20 has a first metal layer 110, composed of generally vertical traces ("vertical" being used as an arbitrary and relative sense of direction). The flex circuit includes a second metal layer 120, composed of generally horizonal traces. The first and second layers are at different depths within the flex circuit 20, so that they may skew over one another without being in electrical contact. An insulating layer 140 separates the first layer 110 from the second layer 120. When it is desired to connect a metal tracing of the first layer 110 with a metal tracing of the second layer 120, a via hole 132 is formed within the insulating layer 140. The via hole 132 is plated so that an electrical connection is formed between the first layer 110 and the second layer 120. The two metal layers are supported by a substrate 130, composed of polyimide or other appropriate material. While multi-layer circuit boards are generally known in the art of electronics, it is believed that the use of a multi-layer flexible circuit board as described above in connection with intraluminal ultrasound imaging or other applications where extreme miniaturization is required is unknown, and is a creative solution to the difficulties of establishing numerous connections between the MUXes, the coaxial cables, the acoustic stack, and associated components. Further, no previous intraluminal ultrasound visualization system known to the inventors has the complex circuitry of the present invention, possibly because no solution to the problem of electrical interconnections was apparent.

Referring to FIGS. 3A, 3B, 8A, and 8B, the flex circuit 20a (or 20b) encircles a catheter portion, the innermost section of which is designated 102a (or 102b), which encircles a guide wire 104a (or 104b) that is substantially at the axis of the probe. The tube may be of polyethylene, or other materials. While not essential to the invention, the tube 102a (or 102b) and guide wire 104a (or 104b) are useful for inserting the flex circuit 20a (or 20b) into a lumen to a desired site. Along with a standard x-ray imaging system, the radio-opaque marker 108a (or 108b), made of platinum-iridium or another radio-opaque material, is useful for allowing a user to determine the precise position of the acoustic stack 30a (or 30b) within a lumen.

Another optional aspect of the invention is described with reference to FIGS. 3C and 3D, wherein the flex circuit is constructed of two distinct sections that are joined during manufacture. Similarly labeled components generally correspond to the "interior" embodiment described above. Thus the two section embodiment has coaxial cables 50c electrically connected to capacitors 70c, in turn electrically connected to MUXes 40c. The combination of the cables 40c, capacitors 70c, and MUXes 40c are referred to herein as the coaxial bundle. The cables 50c, capacitors 70c, and MUXes 40c are electrically interconnected by common connection to a flex circuit section 20c. The coaxial bundle further comprises, or is attached to, a guide wire 104c and catheter tubing 102c.

The MUXes 40c are electrically connected to an acoustic stack 30c. The acoustic stack 30c includes, from the exterior of the device inward, a secondary matching layer 80c, a piezoelectric transducer array 90c, a flex circuit section 22c, and acoustic backing layer 100c. The function of the acoustic stack 30c is substantially identical to the acoustic stack 30a. The stack 30c preferably encloses a radio-opaque marker band 108c.

Figure 3C:
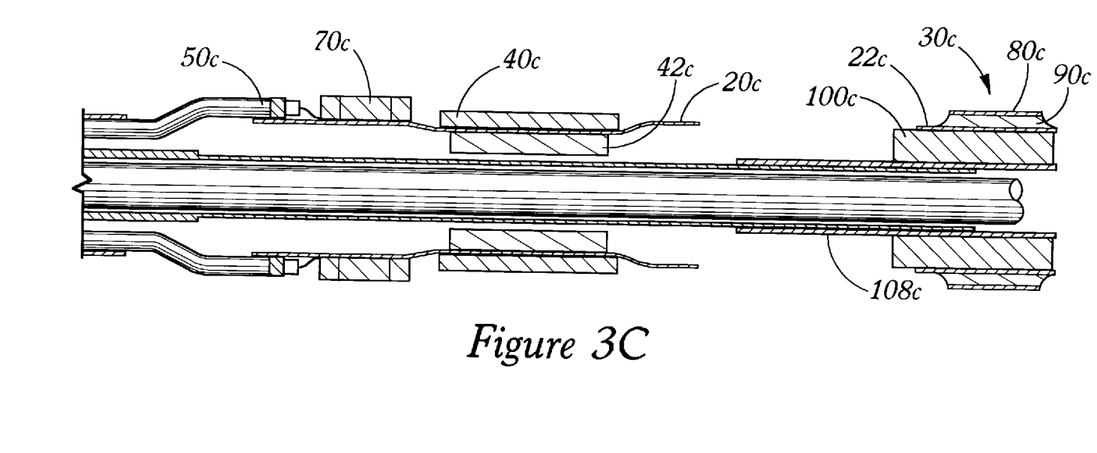
FIG. 3C is a longitudinal sectional view of a transducer array probe according to an aspect of the present invention having a two section flex circuit, before the two sections are joined.
Figure 3D:
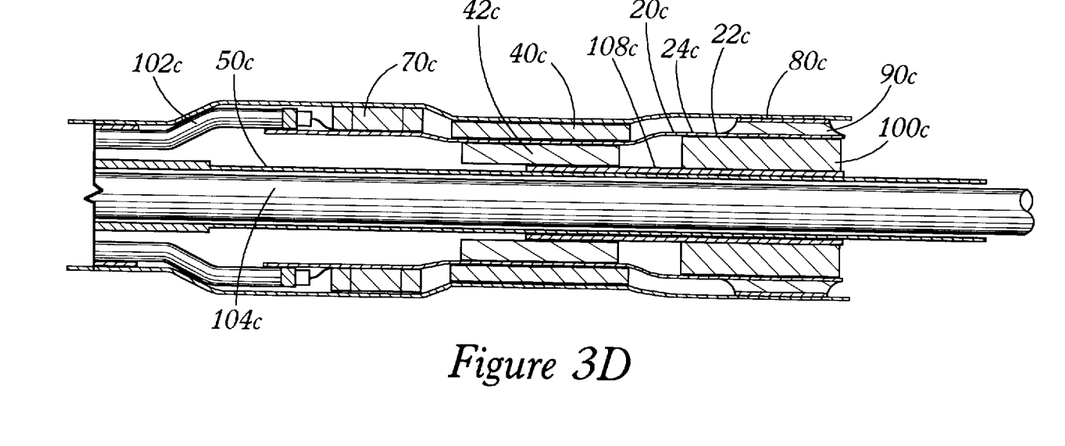
FIG. 3D is a longitudinal sectional view of the transducer array probe of FIG. 3C, after the two sections are joined.

As shown in FIG. 3C, a coaxial bundle and the acoustic stack 30c are manufactured separately from one another. Thereafter, in a later manufacturing step, the bundle and stack 30c are joined together, as shown in FIG. 3D. After joining, the two flex circuit sections 20c, 22c function as one. It is important that the section of the flex circuit 20c initially included within the coaxial bundle is properly electrically connected to the portion of the flex circuit 22c initially within the acoustic stack. Such connection may be accomplished, for example, by placing the flex circuit section 20c adjacent flex circuit section 22c, placing the joined sections in a deposition chamber according to any chemical or physical deposition procedure so that a deposited conductive material (such as gold) connects appropriate circuit sections, thus forming electrical connections therebetween, and separating distinct tracings, such as by laser etching. Thereafter, the array probe structure is similar to the "exterior" embodiment; indeed, the two sections flex may be considered to be a manufacturing process to construct the exterior embodiment.

Several features may be useful, although not required, if the two section embodiment is utilized. It may be desirable to form the radio-opaque marker 108c relatively longer, so that the marker 108c stabilizes the joined flex circuit sections 20c, 22c, and more generally stabilizes the coaxial bundle and the acoustic stack 30c. It may be desirable to include support members 42c beneath the MUXes 40c. The support members 42c are suitably rigid to facilitate the joining of the bundle and stack 30c. As shown, the marker 108c is connected to the support member 42c; however, if the support members 42c are not used or if a shortened marker 108c is used, appropriate connections or modifications can be made.

The joined coaxial bundle and acoustic stack 30c are enclosed by an exterior layer 24c, such as of polyurethane, that serves the identical function as the exterior layer 24a.

The two section flex circuit 20c provides several advantages. The acoustic stack 30c and the coaxial bundle can be manufactured independently of one another. In particular, the dicing of the piezoelectric layer 90c into distinct array elements will not affect the sensitive circuitry of the coaxial bundle, and especially the MUXes 40c. It may be easier to assemble the bundle and stack 30c than to construct a unitary system.

It can be appreciated that the present invention provides an ultrasound imaging array probe that can be situated within a lumen of a body. The probe allows for complicated electronic interconnections, and has a large number of transducers for high quality imaging. As modifications and variations could be made to the above-described embodiment, which is provided for the purpose of illustration and not limitation, it should be understood that the scope of the invention is limited solely by the appended claims and their legal equivalents.

What is claimed is:

1. An ultrasound transducer array probe for an imaging catheter, the probe being generally cylindrical and defining an interior direction towards an axis and an exterior direction away from the axis, the probe comprising:

a flexible circuit substrate having connecting means to physically and electrically receive a plurality of coaxial cables including at least some power supply cables, the flexible circuit substrate supporting two metal layers, each of the metal layers having traces thereon;

a plurality of micro-capacitor structures in electrical communication with at least some of the coaxial cables that are power supply cables;

a plurality of multiplexer/pre-amplifier integrated circuits in electrical communication with the micro-capacitor structures;

a piezoelectric layer comprising a plurality of ultrasound array elements in electrical communication with the integrated circuits, the electrical communication being through at least some of the traces on the metal layers; and an acoustic backing layer acoustically engaged with the piezoelectric elements, the acoustic backing layer being interior with respect to the piezoelectric elements.

2. The array probe of claim 1, wherein the micro-capacitor structures are formed from a combination of discrete capacitors.

3. The array probe of claim 2, wherein the discrete capacitors are aligned with the integrated circuits.

4. The array probe of claim 1, further comprising a primary acoustic matching layer exterior to the piezoelectric layer; and wherein the piezoelectric layer is exterior to the flexible circuit substrate.

5. The array probe of claim 4, wherein the primary acoustic matching layer is an electrical insulator.

6. The array probe of claim 4, wherein the primary acoustic matching layer is an electrical conductor.

7. The array probe of claim 4, further comprising an exterior film layer, the exterior film layer being exterior to the primary acoustic matching layer and being composed of a bio-compatible material.

8. The array probe of claim 7, wherein both the primary acoustic matching layer and the exterior film layer are substantially quarter wave matching layers.

9. The array probe of claim 8, wherein the primary acoustic matching layer has an acoustical impedance of about 7–15 MRayls and the exterior film layer has an acoustical impedance of about 2–6 MRayls.

10. The array probe of claim 8, wherein the exterior film layer is composed of polyurethane.

11. The array probe of claim 8, wherein the exterior film layer comprises polyethylene shrink wrap or filled silicone elastomer.

12. The array probe of claim 8, further comprising a radio-opaque marker interior the piezoelectric layer.

13. The array probe of claim 12, further comprising a guide wire, the guide wire being substantially aligned with the axis of the of the probe and interior the piezoelectric layer.

14. The array probe of claim 8, wherein at least some of the metal traces on each of the two metal layers supported by the flexible circuit substrate are electrically interconnected to at least some of the metal traces on the other metal layer through via holes.

15. The array probe of claim 14, wherein the traces on one of the metal layers are generally vertical and the traces on the other metal layer are generally horizontal, the vertical and horizontal directions being arbitrary with respect to the probe and relative to each other, whereby the traces on the two layers are generally perpendicular with respect to one another.

16. The array probe of claim 15, wherein the two metal layers are separated by an insulating layer.

17. The array probe of claim 4 wherein a portion of said flexible substrate is exterior to the primary acoustic matching layer and is the most exterior layer of the probe, the portion of said flexible substrate serving substantially as a quarter wave matching layer.

18. The array probe of claim 17, wherein the array probe has exactly one matching layer, which is the portion of said flexible substrate.

19. The array probe of claim 18, wherein the portion of said flexible substrate has an acoustical impedance of between about 2.5–7.5 MRayls.

20. The array probe of claim 17, further comprising a second acoustic matching layer, the second acoustic matching layer being substantially a quarter wave matching layer and being situated between the piezoelectric elements and the portion of said flexible substrate forming an acoustic matching layer.

21. The array probe of claim 20, wherein the primary acoustic matching layer has an acoustical impedance of about 7–15 MRayls and the exterior film layer has an acoustical impedance of about 2–6 MRayls.

22. The array probe of claim 20, wherein at least some of the metal traces on each of the two metal layers supported by the flexible circuit substrate are electrically interconnected to at least some of the metal traces on the other metal layer through via holes.

23. The array probe of claim 22, wherein the traces on one of the metal layers are generally vertical and the traces on the other metal layer are generally horizontal, the vertical and horizontal directions being arbitrary with respect to the probe and relative to each other, whereby the traces on the two layers are generally perpendicular with respect to one another.

24. The array probe of claim 23, wherein the two metal layers are separated by an insulating layer.

25. The array probe of claim 1, wherein the flexible circuit substrate is constructed of two distinct sections that are joined during manufacture.

26. The array probe of claim 25, made by a process such that, before the sections are joined, one flex circuit section is electrically connected to the coaxial cables, the micro-capacitor structures, and the multiplexer/pre-amplifier integrated circuits; and the other flex circuit section is electrically connected to the piezoelectric ultrasound array elements.

27. The array probe of claim 26, wherein the two flex circuit sections are joined by depositing a conductor on at least a portion of the flex circuit sections.

28. The array probe of claim 27, wherein the joining of the flex circuit sections includes separating the traces on the flex circuit metal layers.

29. The array probe of claim 25, further comprising a radio-opaque marker extending generally from the piezoelectric array to the multiplexer/pre-amplifier integrated circuits, whereby the joined flex circuit sections are stabilized.

30. The array probe of claim 29, further comprising support members beneath the multiplexer/pre-amplifier integrated circuits.

31. A composition of matter having utility as an acoustic backing layer comprising: a filled urethane compound having an acoustical impedance of between 2.5–6 Mrayl, wherein the urethane is filled with material selected from the class consisting of tungsten trioxide powder, micro-balloons, and combinations thereof.

32. A composition of matter having utility as an acoustic backing layer comprising: a filled urethane compound having an acoustical impedance of between 2.5–6 Mrayl, wherein the compound is filled with tungsten trioxide powder, micro-balloons, and AlN$_3$.

33. The composition of matter of claim 32, wherein the compound consists essentially of the following materials in the approximate following ratio: urethane, 3.08 grams; tungsten trioxide powder, 1.53 g; AlN$_3$ powder, 0.191 g; and micro-balloons, 0.38 g.

* * * * *